(12) United States Patent
Paradies et al.

(10) Patent No.: US 8,324,418 B2
(45) Date of Patent: Dec. 4, 2012

(54) PROCESS FOR HE PRODUCTION OF ORGANIC DITHIOPYROPHOSPHATES

(75) Inventors: Gesa Paradies, Brig (CH); Thomas Riedel, Brig (CH); Christian Schnider, Visp (CH)

(73) Assignee: Lonza Ltd., Basel (CH)

(*) Notice: Subject to any disclaimer, the term of this patent is extended or adjusted under 35 U.S.C. 154(b) by 118 days.

(21) Appl. No.: 13/126,422

(22) PCT Filed: Oct. 21, 2009

(86) PCT No.: PCT/EP2009/007532
§ 371 (c)(1), (2), (4) Date: Apr. 27, 2011

(87) PCT Pub. No.: WO2010/049083
PCT Pub. Date: May 6, 2010

(65) Prior Publication Data
US 2011/0207955 A1    Aug. 25, 2011

(30) Foreign Application Priority Data

Oct. 29, 2008  (EP) .................................. 08018859
Jul. 6, 2009  (EP) .................................. 09008812

(51) Int. Cl.
*C07F 9/17* (2006.01)
(52) U.S. Cl. ........................................... 558/79
(58) Field of Classification Search .................. None
See application file for complete search history.

(56) References Cited

U.S. PATENT DOCUMENTS
5,948,930 A    9/1999    Mayes et al.

FOREIGN PATENT DOCUMENTS
| CH | 603674 | 8/1978 |
| CH | 603674 A5 | 8/1978 |
| NL | 7508884 A | 2/1976 |

OTHER PUBLICATIONS

Koutu et al., Indian Journal of Fibre&Textile Research, 1996, 21, 140-142.*

* cited by examiner

*Primary Examiner* — Sun Jae Loewe
(74) *Attorney, Agent, or Firm* — McDonnell Boehnen Hulbert & Berghoff LLP

(57) ABSTRACT

Organic dithiopyrophosphates of formula wherein $R^1$, $R^2$, $R^3$, $R^4$ and $R^5$ independently are hydrogen, $C_{1-4}$ alkyl, chloromethyl or bromomethyl, are prepared in a two-step process from the corresponding 1,3-diols and thiophosphoryl chloride, using 3-methylpyridine both as solvent and as base.

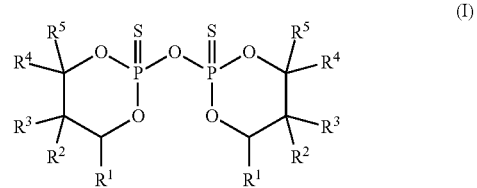

(I)

4 Claims, No Drawings

PROCESS FOR HE PRODUCTION OF ORGANIC DITHIOPYROPHOSPHATES

This application is a US national phase of International Application No. PCT/EP2009/007532 filed on Oct. 21, 2009, the disclosure of which is incorporated herein by reference in its entirety.

The invention relates to an improved process for the production of organic dithiopyrophosphates of formula

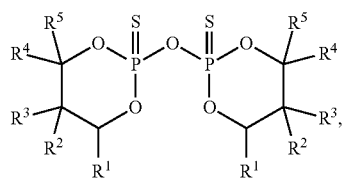
(I)

wherein $R^1$, $R^2$, $R^3$, $R^4$ and $R^5$ independently are hydrogen, $C_{1-4}$ alkyl, chloromethyl or bromomethyl.

Compounds of formula I are known as flame retardants for polymers, in particular for textile applications, see e.g. NL 7508884 A.

Known processes for the production of the organic dithiopyrophosphates of formula I involve the reaction of a 1,3-diol with thiophosphoryl chloride ($PSCl_3$) to give a 2-chloro-2-thioxo-1,3,2-dioxaphosphorinane intermediate which is isolated and then reacted with an oxide, hydroxide, carbonate or hydrogencarbonate of an alkali or alkaline earth metal (most preferably calcium oxide) in the presence of a tertiary organic base (CH 625 806) or with water (NL 7508884 A). The prior art processes require different solvents or solvent mixtures for the two reaction steps and isolation of the intermediate 2-chloro-2-thioxo-1,3,2-dioxaphosphorinane. Moreover, when calcium oxide is used in the second step this results in the formation of calcium chloride which has to separated and disposed of.

It is an object of the present invention to provide a simplified process for the production of the organic dithiopyrophosphates of formula I that does not require different solvents and does not result in the formation of inorganic salts as byproducts.

According to the invention, this object has been accomplished by the process defined in claim 1. Applicants have found that organic dithiopyrophosphates of formula

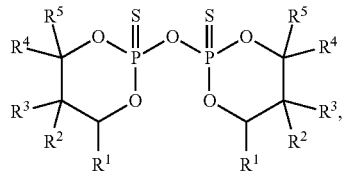
(I)

wherein $R^1$, $R^2$, $R^3$, $R^4$ and $R^5$ independently are hydrogen, $C_{1-4}$ alkyl, chloromethyl or bromomethyl,
can be produced by a process comprising the steps of
(i) reacting a 1,3-diol of formula

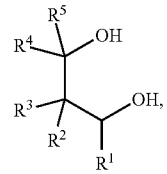
(II)

wherein $R^1$, $R^2$, $R^3$, $R^4$ and $R^5$ are as defined above,
to obtain a 2-chloro-2-thioxo-1,3,2-dioxaphosphorinane of formula

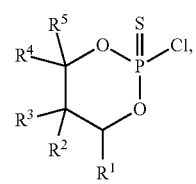
(III)

wherein $R^1$, $R^2$, $R^3$, $R^4$ and $R^5$ are as defined above, and
(ii) partially hydrolyzing the 2-chloro-2-thioxo-1,3,2-dioxaphosphorinane (III) with water in the presence of a base to obtain the corresponding dithiopyrophosphate (I),
wherein 3-methylpyridine is used both as an organic solvent and as a base in steps (i) and (ii).

Here and hereinbelow, $C_{1-4}$ alkyl is to be understood to mean any linear or branched alkyl group having one to four carbon atoms, in particular methyl, ethyl, propyl, isopropyl, butyl, isobutyl, sec-butyl and tent-butyl.

As a solvent, 3-methylpyridine may be used alone or in a mixture with another solvent. In a preferred embodiment of the process of the invention, 3-methylpyridine is used as the sole solvent in both steps.

It is also within the scope of the invention to use 3-methylpyridine alone or in combination with other bases. In a preferred embodiment, 3-methylpyridine is used as the sole base in both steps.

In a particularly preferred embodiment, both reaction steps are conducted as a one-pot reaction without isolating the 2-chloro-2-thioxo-1,3,2-dioxaphosphorinane intermediate (III).

In an even more preferred embodiment, in step (i) the thiophosphoryl chloride is slowly added to a solution of the 1,3-diol (II) in 3-methylpyridine and in step (ii) the water is slowly added to the reaction mixture obtained in step (i). Surprisingly it has been found that it is possible to shorten the process of the invention by starting the addition of water before the addition of thiophosphoryl chloride is completed. Thus it is possible to have steps (i) and (ii), at least in part, take place simultaneously in that the hydrolysis of the 2-chloro-2-thioxo-1,3,2-dioxaphosphorinane intermediate (III) commences before the whole 1,3-diol starting material (II) is reacted. The addition of water may be started after one half, one third, or even less of the thiophosphoryl chloride has been added.

In an especially preferred embodiment, $R^1$, $R^4$ and $R^5$ in formulas I, II and III are hydrogen atoms at each occurrence and both $R^2$ and $R^3$ are methyl groups.

Steps (i) and (ii) are advantageously conducted at reaction temperatures between −10° C. and 100° C., preferably between 20° C. and 100° C. or between 40° C. and 80° C. If both steps are conducted separately, the temperature in the first step is preferably between 20° C. and 50° C., and in the second step between 50° C. and 60° C. If thiophosphoryl chloride and water are added simultaneously or in overlapping periods of time, the reaction is preferably started at 20° C. to 50° C. and completed at 50° C. to 60° C. Since the reaction is exothermic, the reaction temperature increase can—at least in part—be achieved by utilizing the heat of reaction.

Both reaction steps can be conducted in relatively concentrated solutions, preferably using between 5 mol and 10 mol of 3-methylpyridine per mol of 1,3-diol (II) or thiophosphoryl chloride. Since 3 mol of 3-methylpyridine per mol of thiophosphoryl chloride are required as base to bind the hydrogen chloride formed in steps (i) (2 mol of HCl) and (ii) (1 mol of HCl), the remaining amount of between 2 mol and 7 mol of 3-methylpyridine that can serve as solvent is remarkably small. Depending on the temperature, in particular the temperature in step (ii), and the amount of 3-methylpyridine used as solvent, the 3-methylpyridinium chloride is obtained in solid or liquid (i.e., melt or concentrated solution) form.

The work-up of the reaction mixture obtained after step (ii) can be performed in a simple manner by adding an amount of water sufficient to dissolve the 3-methylpyridinium chloride formed in reaction steps (i) and (ii) and isolating the dithiopyrophosphate (I) by filtration. In case the 3-methylpyridinium chloride is obtained in liquid form the work-up can be further simplified by filtering off the product before addition of water.

After filtration the dithiopyrophosphate is advantageously washed with water to remove residual 3-methylpridine and 3-methylpyridinium chloride. It has been found that the washing process can be facilitated by addition of a surfactant to the washing water. Preferred surfactants are nonionic surfactants such as triethanolamine polyglycol ethers. Suitable compounds are commercially available, e.g. under the brand name Stokomin® (Bozzetto GmbH, Krefeld, Germany).

In a preferred embodiment the 3-methylpyridine is recovered from the filtrate and recycled.

More preferably, the recovery is conducted as follows: Water and an alkali hydroxide, most preferably sodium hydroxide, are added to the filtrate to liberate the 3-methylpyridine free base from the 3-methylpyridinium chloride formed in reaction steps (i) and (ii), whereby an aqueous phase containing dissolved alkali chloride and an organic phase comprising 3-methylpyridine and some dissolved water are formed. The aqueous phase is separated off and essentially pure 3-methylpyridine is obtained by rectification of the organic phase, where the recovered 3-methylpyridine is separated from the dissolved water that accumulates (as such or as azeotropic mixture with 3-methylpyridine) in the head of the rectification column. This recovery and recycling process is particularly easy when 3-methylpyridine is used as sole solvent.

The following non-limiting example illustrates the process of the invention.

EXAMPLE 1

2,2'-Oxybis-(5,5-dimethyl-1,3,2-dioxaphosphorinane)-2,2'-disulfide (I, $R^1=R^4=R^5=H$, $R^2=R^3=CH_3$)

A 1 L stirred reactor was charged with 3-methylpyridine (600 g, 6.44 mol) and 2,2-di-methyl-1,3-propanediol (104.5 g, 1 mol). The mixture was warmed to 45° C. and thiophosphoryl chloride (PSCl$_3$, 98%, 172.9 g, 1 mol) was added over 4 h while the temperature was not allowed to exceed 50° C. After another 30 min, water (9.5 g, 0.53 mol) was added dropwise at 45-50° C. The mixture was then warmed to 60° C. and kept at that temperature for 15 h. Water (160 g) was then added to dissolve the 3-methylpyridinium chloride formed in the reaction. The product was isolated by filtration, washed with water several times and sucked dry. To facilitate the removal of residual 3-methylpyridine, 0.015 wt. % Stokomin® MI 07 surfactant (triethanolamine tris-alkylpolyglycol ether) was added to the washing water.

Yield: 75%.

EXAMPLE 2

2,2'-Oxybis-(5,5-dimethyl-1,3,2-dioxaphosphorinane)-2,2'-disulfide (I, $R^1=R^4=R^5=H$, $R^2=R^3=CH_3$)

A 1 L stirred reactor was charged with 3-methylpyridine (600 g, 6.44 mol) and 2,2-di-methyl-1,3-propanediol (105.2 g, =1 mol). The mixture was warmed to 50° C. and thiophosphoryl chloride (PSCl$_3$, 167.5 g, =1 mol) was added over 3 h while the temperature was not allowed to exceed 50° C. One hour after the start of the thiophosphoryl chloride addition the continuous addition of water (9.2 g, 0.51 mol) over a period of 5.5 h was started and after completion of the thiophosphoryl chloride addition the temperature was increased to 60° C. within 1 h. After completion of the water addition, stirring was continued overnight (ca. 16 h) at 60° C. Water (180 g) was then added within about 2 min to dissolve the 3-methylpyridinium chloride formed in the reaction. The product was isolated by filtration and washed with the filtrate.

Yield: 222 g moist product, content (HPLC assay): 66.1%, corresponding to 84.6% yield.

The invention claimed is:

1. A process for the production of an organic dithiopyrophosphate of formula

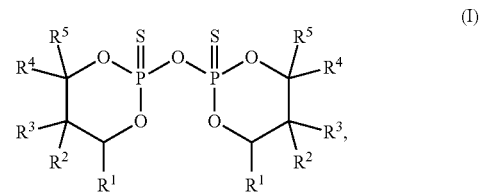

(I)

wherein $R^1$, $R^2$, $R^3$, $R^4$ and $R^5$ independently are hydrogen, $C_{1-4}$ alkyl, chloromethyl or bromomethyl, comprising the steps of
  (i) reacting a 1,3-diol of formula

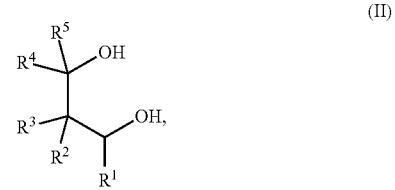

(II)

wherein $R^1$, $R^2$, $R^3$, $R^4$ and $R^5$ are as defined above, in an organic solvent with thiophosphoryl chloride in the presence of a base, to obtain a 2-chloro-2-thioxo-1,3,2-dioxaphosphorinane of formula

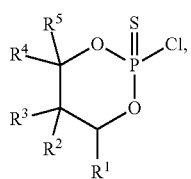

(III)

wherein $R^1$, $R^2$, $R^3$, $R^4$ and $R^5$ are as defined above, and (ii) partially hydrolyzing the 2-chloro-2-thioxo-1,3,2-dioxaphosphorinane (III) with water in the presence of a base to obtain the corresponding dithiopyrophosphate (I), characterized in that 3-methylpyridine is used both as an organic solvent and as a base in steps (i) and (ii), and wherein steps (i) and (ii) are conducted as a one-pot reaction without isolating the 2-chloro-2-thioxo-1,3,2-dioxaphosphorinane intermediate (III), and wherein in step (i) the thiophosphoryl chloride is added to a solution of the 1,3-diol (II) in 3-methylpyridine and in step (ii) the water is added to the reaction mixture obtained in step (i); and wherein the addition of water is started before the addition of thiophosphoryl chloride is completed.

2. The process of claim 1, wherein $R^1$, $R^4$ and $R^5$ at each occurrence are hydrogen atoms and $R^2$ and $R^3$ are methyl groups.

3. The process of claim 1, wherein, after isolating the dithiopyrophosphate (I) by filtration, the 3-methylpyridine is recovered from the filtrate and recycled.

4. The process of claim 3, wherein the 3-methylpyridine recovery comprises the steps of adding water and an alkali hydroxide to the filtrate to liberate the 3-methylpyridine free base from the 3-methylpyridinium chloride formed in reaction steps (i) and (ii), thus forming an aqueous phase containing dissolved alkali chloride and an organic phase containing 3-methylpyridine and dissolved water; separating off the aqueous phase; and rectification of said organic phase to obtain essentially pure 3-methylpyridine.

* * * * *

UNITED STATES PATENT AND TRADEMARK OFFICE
CERTIFICATE OF CORRECTION

| | | |
|---|---|---|
| PATENT NO. | : 8,324,418 B2 | Page 1 of 1 |
| APPLICATION NO. | : 13/126422 | |
| DATED | : December 4, 2012 | |
| INVENTOR(S) | : Gesa Paradies, Thomas Riedel and Christian Schnider | |

It is certified that error appears in the above-identified patent and that said Letters Patent is hereby corrected as shown below:

Title Page, at item (54) of the cover sheet:

please delete "HE" and insert --THE--.

Signed and Sealed this
Twenty-ninth Day of January, 2013

David J. Kappos
*Director of the United States Patent and Trademark Office*

UNITED STATES PATENT AND TRADEMARK OFFICE
CERTIFICATE OF CORRECTION

PATENT NO. : 8,324,418 B2  
APPLICATION NO. : 13/126422  
DATED : December 4, 2012  
INVENTOR(S) : Gesa Paradies, Thomas Riedel and Christian Schnider It is certified that error appears in the above-identified patent and that said Letters Patent is hereby corrected as shown below:

Title Page, at item (54) and at Column 1, line 1, Title please delete "HE" and insert --THE--.

This certificate supersedes the Certificate of Correction issued January 29, 2013.

Signed and Sealed this  
Nineteenth Day of February, 2013

Teresa Stanek Rea  
*Acting Director of the United States Patent and Trademark Office*